United States Patent
Watson et al.

(10) Patent No.: US 10,155,799 B2
(45) Date of Patent: Dec. 18, 2018

(54) CHROMATOGRAPHY PROCESS FOR PURIFICATION OF INSULIN AND INSULIN ANALOGS

(71) Applicant: Merck Sharp & Dohme Corp., Rahway, NJ (US)

(72) Inventors: Douglas S. Watson, Harrisonburg, VA (US); Allison D. Ortigosa, Harrisonburg, VA (US); Michael A. Rauscher, Garwood, NJ (US); Kathryn M. Story, Harrisonburg, VA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/327,096

(22) PCT Filed: Jul. 16, 2015

(86) PCT No.: PCT/US2015/040675
§ 371 (c)(1),
(2) Date: Jan. 18, 2017

(87) PCT Pub. No.: WO2016/014325
PCT Pub. Date: Jan. 28, 2016

(65) Prior Publication Data
US 2017/0174737 A1 Jun. 22, 2017

Related U.S. Application Data

(60) Provisional application No. 62/026,719, filed on Jul. 21, 2014.

(51) Int. Cl.
| | | |
|---|---|---|
| *B01D 15/18* | (2006.01) | |
| *C07K 14/62* | (2006.01) | |
| *B01D 15/32* | (2006.01) | |
| *B01D 15/36* | (2006.01) | |
| *C07K 1/18* | (2006.01) | |
| *C07K 1/20* | (2006.01) | |
| *B01D 15/38* | (2006.01) | |

(52) U.S. Cl.
CPC .......... *C07K 14/62* (2013.01); *B01D 15/1878* (2013.01); *B01D 15/327* (2013.01); *B01D 15/363* (2013.01); *B01D 15/3847* (2013.01); *C07K 1/18* (2013.01); *C07K 1/20* (2013.01)

(58) Field of Classification Search
None
See application file for complete search history.

(56) References Cited

U.S. PATENT DOCUMENTS

| | | | |
|---|---|---|---|
| 2,538,018 A * | 1/1951 | Krayenbuhl | C07K 14/62 514/6.4 |
| 4,129,560 A | 12/1978 | Zoltobrocki | |
| 4,677,192 A | 6/1987 | Obermeier et al. | |
| 5,245,008 A | 9/1993 | Dickhardt et al. | |
| 5,621,073 A | 4/1997 | Dickhardt et al. | |
| 5,977,297 A | 11/1999 | Obermeier et al. | |
| 6,001,604 A * | 12/1999 | Hartman | C07K 14/62 435/68.1 |
| 6,710,167 B1 | 3/2004 | Sievers et al. | |
| 7,608,583 B2 | 10/2009 | Sahib et al. | |
| 7,867,784 B2 * | 1/2011 | Engstrand | B01D 15/327 436/528 |
| 2004/0029164 A1 | 2/2004 | Ransohoff | |
| 2013/0330751 A1 | 12/2013 | Mallender et al. | |

FOREIGN PATENT DOCUMENTS

| | | |
|---|---|---|
| WO | 2012104339 | 8/2012 |
| WO | 2012152439 | 11/2012 |
| WO | 2014099577 | 6/2014 |

OTHER PUBLICATIONS

Liu et al., "A Weak Anion-Exchange/Reversed-Phase Mixed-Mode HPLC Column and its Applications," posted on Oct. 1, 2007, available at http://www.americanlaboratory.com/913-Technical-Articles/1454-A-Weak-Anion-Exchange-Reversed-Phase-Mixed-Mode-HPLC-Column-and-its-Applications/ accessed on Jul. 26, 2017 8:34:22 AM.*
Sigma-Aldrich product information publication for Sepharose_Ion Exchange Media, Sigma-Aldrich Co. (2012) available at https://www.sigmaaldrich.com/content/dam/sigma-aldrich/docs/Sigma/Product_Information_Sheet/dff100pis.pdf, accessed on Jul. 26, 2017.*
Bernardi et al., Journal of Chromatography A (2013) 1283, 46-52.*
Yan et al., Protein Science (2003) 12, 768-775.*
EMDMillipore, Lichrosphere 100 RP-8 column (Merck), see http://www.emdmillipore.com/US/en/product/LiChrospher-100-RP-8-5-m-LiChroCART-250-4,MDA_CHEM-150832; accessed on Jan. 21, 2018; pp. 1-2 (Year: 2018).*
Karkov et al., Methods development in multimodal chromatography with mobilephase modifiers using the steric mass action model, J. Chromatography A, 1318: 149-155 (2013).
Zhu et al., Developing a strong anion exchange/RP (SAX/RP) 2D LC system for high-abundance proteins depletion in human plasma, Proteomics, vol. 12, 2012, pp. 3451-3463.
Kroeff et al., Production scale purification of biosynthetic human insulin by reversed-phase high-performance liquid chromatography, Journal of Chromatography, vol. 461, 1989, pp. 45-61.

* cited by examiner

*Primary Examiner* — Lianko G Garyu
(74) *Attorney, Agent, or Firm* — John David Reilly; Laura M. Ginkel

(57) ABSTRACT

A process is described for purifying insulin and insulin analogs that comprises use of two or more orthogonal chromatographic purification steps in tandem following enzymatic digestion of the propeptide-insulin precursor to remove specific product impurities, improve process consistency, and increase process redundancy in the purification of the insulin or insulin analog, e.g., insulin lispro.

4 Claims, 1 Drawing Sheet
Specification includes a Sequence Listing.

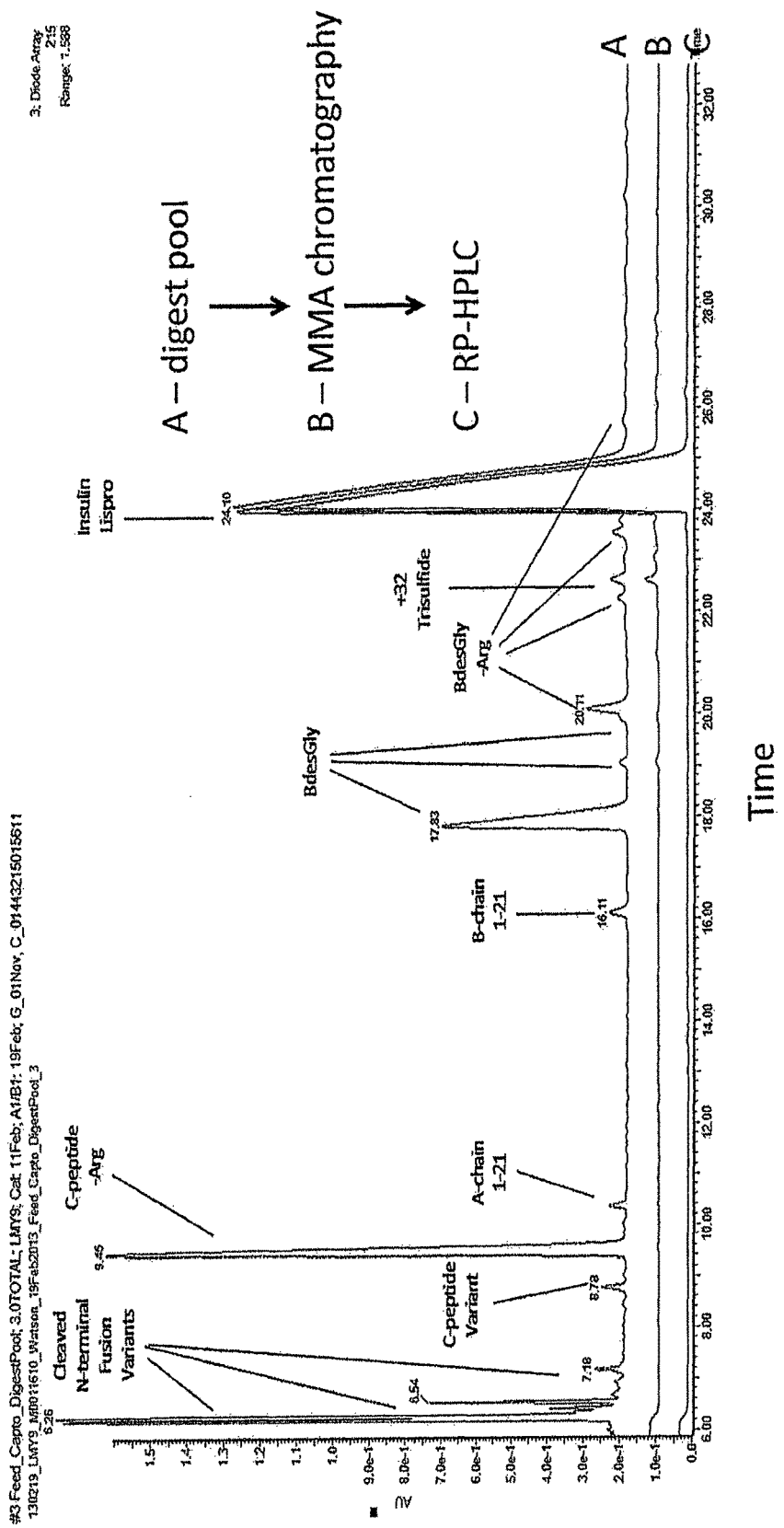

SEQUENCE LISTING

```
<160> NUMBER OF SEQ ID NOS: 2

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30
```

CHROMATOGRAPHY PROCESS FOR PURIFICATION OF INSULIN AND INSULIN ANALOGS

CROSS REFERENCE TO RELATED APPLICATIONS

This application is a § 371 National Stage entry of PCT/US2015/040675, filed Jul. 16, 2015, and claims benefit of U.S. Provisional Application No. 62/026,719, filed Jul. 21, 2014, both of which are herein incorporated by reference in their entirety.

BACKGROUND OF THE INVENTION (1) Field of the Invention

The present invention relates to a process for purifying insulin and insulin analogs that comprises use of two or more orthogonal chromatographic purification steps in tandem following enzymatic digestion of the propeptide-insulin precursor to remove specific product impurities, improve process consistency, and increase process redundancy in the purification of the insulin or insulin analog, e.g., insulin lispro.

(2) Description of Related Art

Precursor insulin or insulin analogue molecules produced in prokaryote host cells such as *E. coli* or lower eukaryote host cells such as *Saccharomyces cerevisiae* or *Pichia pastoris* are enzymatically cleaved in vitro to remove the connecting peptide joining the B-chain peptide to the A-chain peptide and the N-terminal propeptide to produce insulin or insulin analogue heterodimers. The enzymatic cleavage of precursor insulin or insulin analogue molecules is achieved by digestion with trypsin, carboxypeptidase B, lysC, or combinations thereof. However, the enzymatic digests introduce impurities such as the three amino acid B-chain truncate (des-Thr), deamidoinsulin, arginine-insulin and diarginine-insulin, and insulin ethyl ester.

A key challenge with the purification of insulin (and other insulin analogs) is the downstream removal of product related impurities arising from miscleavage or insufficient cleavage of the propeptide-insulin precursor molecule during the enzymatic digest. Such product impurities include N-terminal propeptide leader and/or signal sequences, C-peptide, dipeptides, aggregated insulin, deamidated insulin, miscleaves, misfolds, and any remaining proinsulin. A significant challenge in the purification of insulin stems from the similarity in chemical structure between insulin and its product-related impurities, which may differ by a single amino acid, requiring selectivity beyond that offered by traditional ion-exchange resins. Additionally, the presence of host cell protein, DNA, and proteolytic enzymes can complicate the purification further by necessitating higher binding capacities and the addition of multiple wash steps.

The following U.S. patents disclose process for purifying proteins or insulins by chromatography: U.S. Pat. Nos. 5,245,008; 4,677,192; 4,129,560; 6,710,167; 5,977,297; and 5,621,073. Karkov et al disclose in J. Chromatography A 1318: 149-155 (2013) a multimodal chromatography method for bind and elute separation of insulin.

BRIEF SUMMARY OF THE INVENTION

The present invention provides a process for purifying insulin or insulin analogs following enzymatic digestion of properly folded propeptide-insulin or insulin analog precursor comprising two orthogonal chromatographic purification steps in tandem following the enzyme digestion. The process separates the properly folded propeptide-insulin or insulin analog precursor from process-related impurities such as N-terminal propeptide leader and/or signal sequences, C-peptide, dipeptides, aggregated insulin, deamidated insulin, miscleaves, misfolds, and any remaining proinsulin. The process improves process consistency and increases process redundancy in the purification of the properly folded insulin or insulin analog. The process may be used to purify properly folded native insulin or insulin analogs such as pI-shifted insulin analogs, for example, insulin glargine; insulin aspart; insulin glulisine, insulin, $21^A$-glycine-$30^B$-L-arginine; insulin, $21^A$-glycine; insulin $21^A$-glycine-des-$30^B$-threonine; or insulin, des-$30^B$-threonine. The process has been exemplified with insulin lispro as a heterodimer but may be used to purify properly folded single-chain insulin analogs.

Therefore, the present invention provides a process for isolating properly folded insulin or insulin analog from an aqueous mixture comprising the properly folded insulin or insulin analog and impurities, wherein the process comprises subjecting the aqueous mixture to two orthogonal chromatography purification steps in tandem to separate the isolated properly folded insulin or insulin analog from the related impurities.

In particular embodiments of the above process, the two orthogonal chromatography purification steps in tandem comprise a chromatography step that separates molecules based upon charge and a chromatography step that separates molecules based upon hydrophobic interactions. In particular embodiments, the chromatography step that separates molecules based upon charge is selected from anion exchange (AEX) chromatography and mixed mode anion exchange (MMA) chromatography. In particular embodiments, the chromatography step that separates molecules based upon hydrophobic interactions is selected from reverse phase high pressure liquid chromatography (RP-HPLC) and hydrophobic interaction chromatography (HIC).

In particular embodiments of the above process, the chromatography step that separates molecules based upon charge is selected from anion exchange (AEX) chromatography and mixed mode anion exchange (MMA) chromatography and the chromatography step that separates molecules based upon hydrophobic interactions is selected from reverse phase high performance liquid chromatography (RP-HPLC) and hydrophobic interaction chromatography (HIC). In particular embodiments, the two orthogonal chromatography purification steps in tandem comprise an MMA chromatography step and an RP-HPLC step.

In particular embodiments, the MMA chromatography is performed with a resin comprising cross-linked agarose conjugated to N-benzyl-N-methyl ethanolamine. In particular embodiments, the AEX chromatography is performed with a resin comprising cross-linked agarose conjugated to DEAE.

In a further embodiment, the MMA or AEX chromatography comprises applying to an MMA or AEX chromatography matrix an aqueous solution in which properly folded precursor insulin or insulin analog has been enzymatically digested to produce the properly folded insulin or insulin analog; washing the MMA or AEX chromatography matrix with a first wash solution comprising a buffer at a basic pH and then washing the MMA or AEX chromatography matrix with a second wash solution comprising a buffer at an acidic pH greater than or higher than the pH capable of eluting the properly folded insulin or insulin analog from the MMA or AEX chromatography matrix; and eluting the properly folded insulin or insulin analog from the MMA or AEX chromatography matrix with an eluting solution comprising a buffer at an acidic pH sufficient to elute the properly folded insulin or insulin analog from the MMA or AEX chromatography matrix to provide the first mixture.

In particular embodiments, the first wash buffer has a pH of about 7.8 to 8.2 or about 8.0; the second wash buffer has a pH of about 8.8 to 5.2 or about 5.0; and the eluting solution buffer has a pH of about 3.4 to 3.6 or about 3.5.

In particular embodiments, the RP-HPLC is performed with a silica-based reverse phase resin in the presence of a water miscible organic modifier.

In a further embodiment, the RP-HPLC comprises a linear gradient of the water miscible organic modifier at an elevated temperature to provide a mixture comprising the isolated properly folded insulin or insulin analog substantially free of process impurities.

In a particular embodiment, the RP-HPLC comprises a linear gradient comprising the water miscible organic modifier increasing in a concentration from about 13 to 15 percent by volume to about 25 to 27 percent by volume.

In a particular embodiment, the RP-HPLC matrix comprises a linear gradient comprising the water miscible organic modifier increasing in a concentration from about 13 to 17 percent by volume to about 18 to 19 percent by volume.

In a particular embodiment, the RP-HPLC matrix comprises a linear gradient comprising the water miscible organic modifier increasing in a concentration from about 16.5 to 17.5 percent by volume to about 18 to 19 percent by volume.

In a particular embodiment, the RP-HPLC matrix comprises a first volume of a first linear gradient of the water miscible organic modifier increasing in concentration from about 13 to 17 percent by volume and a second volume of a second linear gradient from about 17 to 18.5 percent by volume of the water miscible organic modifier to provide a mixture of the properly folded insulin or insulin analog.

In a particular embodiment, the RP-HPLC has an outlet temperature greater than room temperature or between 30° C. to 50° C.; or greater than 30° C.; greater than 40° C.; or a temperature between 40° C. to 46° C.; or about 43° C.

In a particular embodiment, the water miscible organic modifier is isopropanol.

The present invention further provides a process for isolating properly folded insulin or insulin analog from an aqueous mixture comprising the properly insulin or insulin analog and impurities, wherein the process comprises (a) performing a chromatography that separates molecules based upon charge with the aqueous mixture to yield a first mixture comprising the insulin or insulin analog; and (b) performing a chromatography step that separates molecules based upon hydrophobic interactions to provide a second mixture comprising the isolated properly folded insulin or insulin analog.

In particular embodiments of the above process, the chromatography step that separates molecules based upon charge is selected from anion exchange (AEX) chromatography and mixed mode anion exchange (MMA) chromatography and the chromatography step that separates molecules based upon hydrophobic interactions is selected from reverse phase high performance liquid chromatography (RP-HPLC) and hydrophobic interaction chromatography (HIC). In particular embodiments, the two orthogonal chromatography purification steps in tandem comprise an MMA chromatography step and an RP-HPLC step.

In particular embodiments, the MMA chromatography is performed with a resin comprising cross-linked agarose conjugated to N-benzyl-N-methyl ethanolamine. In particular embodiments, the AEX chromatography is performed with a resin comprising cross-linked agarose conjugated to DEAE.

In a further embodiment, the MMA or AEX chromatography comprises applying to an MMA or AEX chromatography matrix an aqueous solution in which properly folded precursor insulin or insulin analog has been enzymatically digested to produce the properly folded insulin or insulin analog; washing the MMA or AEX chromatography matrix with a first wash solution comprising a buffer at a basic pH and then washing the MMA or AEX chromatography matrix with a second wash solution comprising a buffer at an acidic pH greater than or higher than the pH capable of eluting the properly folded insulin or insulin analog from the MMA or AEX chromatography matrix; and eluting the properly folded insulin or insulin analog from the MMA or AEX chromatography matrix with an eluting solution comprising a buffer at an acidic pH sufficient to elute the properly folded insulin or insulin analog from the MMA or AEX chromatography matrix to provide the first mixture.

In particular embodiments, the first wash buffer has a pH of about 7.8 to 8.2 or about 8.0; the second wash buffer has a pH of about 8.8 to 5.2 or about 5.0; and the eluting solution buffer has a pH of about 3.4 to 3.6 or about 3.5.

In particular embodiments, the RP-HPLC is performed with a silica-based reverse phase resin in the presence of a water miscible organic modifier.

In a further embodiment, the RP-HPLC comprises a linear gradient of the water miscible organic modifier at an elevated temperature to provide a mixture comprising the isolated properly folded insulin or insulin analog substantially free of process impurities.

In a particular embodiment, the RP-HPLC comprises a linear gradient comprising the water miscible organic modifier increasing in a concentration from about 13 to 15 percent by volume to about 25 to 27 percent by volume.

In a particular embodiment, the RP-HPLC matrix comprises a linear gradient comprising the water miscible organic modifier increasing in a concentration from about 13 to 17 percent by volume to about 18 to 19 percent by volume.

In a particular embodiment, the RP-HPLC matrix comprises a linear gradient comprising the water miscible organic modifier increasing in a concentration from about 16.5 to 17.5 percent by volume to about 18 to 19 percent by volume.

In a particular embodiment, the RP-HPLC matrix comprises a first volume of a first linear gradient of the water miscible organic modifier increasing in concentration from about 13 to 17 percent by volume and a second volume of a second linear gradient from about 17 to 18.5 percent by volume of the water miscible organic modifier to provide a mixture of the properly folded insulin or insulin analog.

In a particular embodiment, the RP-HPLC has an outlet temperature greater than room temperature or between 30° C. to 50° C.; or greater than 30° C.; greater than 40° C.; or a temperature between 40° C. to 46° C.; or about 43° C.

In a particular embodiment, the water miscible organic modifier is isopropanol.

The present invention further provides a process for isolating properly folded insulin or insulin analog from an aqueous mixture comprising the properly insulin or insulin analog and impurities, wherein the process comprises (a) performing a mixed mode anion exchange (MMA) chromatography with the aqueous mixture to yield a first mixture comprising the insulin or insulin analog; and (b) performing a reverse phase high performance liquid chromatography (RP-HPLC) on the first mixture in the presence of a water miscible organic modifier to provide a second mixture comprising the isolated properly folded insulin or insulin analog.

In particular embodiments, the MMA chromatography is performed with a resin comprising cross-linked agarose conjugated to N-benzyl-N-methyl ethanolamine.

In a further embodiment, the MMA chromatography comprises applying to an MMA chromatography matrix an aqueous solution in which properly folded precursor insulin or insulin analog has been enzymatically digested to produce the properly folded insulin or insulin analog; washing the MMA chromatography matrix with a first wash solution comprising a buffer at a basic pH and then washing the MMA chromatography matrix with a second wash solution comprising a buffer at an acidic pH greater than or higher than the pH capable of eluting the properly folded insulin or insulin analog from the MMA chromatography matrix; and eluting the properly folded insulin or insulin analog from the MMA chromatography matrix with an eluting solution comprising a buffer at an acidic pH sufficient to elute the properly folded insulin or insulin analog from the MMA chromatography matrix to provide the first mixture.

In particular embodiments, the first wash buffer has a pH of about 7.8 to 8.2 or about 8.0; the second wash buffer has a pH of about 8.8 to 5.2 or about 5.0; and the eluting solution buffer has a pH of about 3.4 to 3.6 or about 3.5.

In particular embodiments, the RP-HPLC is performed with a silica-based reverse phase resin in the presence of a water miscible organic modifier.

In a further embodiment, the RP-HPLC comprises a linear gradient of the water miscible organic modifier at an elevated temperature to provide a mixture comprising the isolated properly folded insulin or insulin analog substantially free of process impurities.

In a particular embodiment, the RP-HPLC comprises a linear gradient comprising the water miscible organic modifier increasing in a concentration from about 13 to 15 percent by volume to about 25 to 27 percent by volume.

In a particular embodiment, the RP-HPLC matrix comprises a linear gradient comprising the water miscible organic modifier increasing in a concentration from about 13 to 17 percent by volume to about 18 to 19 percent by volume.

In a particular embodiment, the RP-HPLC matrix comprises a linear gradient comprising the water miscible organic modifier increasing in a concentration from about 16.5 to 17.5 percent by volume to about 18 to 19 percent by volume.

In a particular embodiment, the RP-HPLC matrix comprises a first volume of a first linear gradient of the water miscible organic modifier increasing in concentration from about 13 to 17 percent by volume and a second volume of a second linear gradient from about 17 to 18.5 percent by volume of the water miscible organic modifier to provide a mixture of the properly folded insulin or insulin analog.

In a particular embodiment, the RP-HPLC has an outlet temperature greater than room temperature or between 30° C. to 50° C.; or greater than 30° C.; greater than 40° C.; or a temperature between 40° C. to 46° C.; or about 43° C.

In a particular embodiment, the water miscible organic modifier is isopropanol.

The present invention further provides a process for purifying a properly folded insulin or insulin analog from process impurities, the process comprising (a) applying to a mixed mode anion exchange (MMA) chromatography matrix an aqueous solution in which properly folded precursor insulin or insulin analog has been enzymatically digested to produce the properly folded insulin or insulin analog; (b) washing the MMA chromatography matrix with a first wash solution comprising a buffer at a basic pH and then washing the MMA chromatography matrix with a second wash solution comprising a buffer at an acidic pH greater than or higher than the pH capable of eluting the properly folded insulin or insulin analog from the MMA chromatography matrix; (c) eluting the properly folded insulin or insulin analog from the MMA chromatography matrix with an eluting solution comprising a buffer at an acidic pH sufficient to elute the properly folded insulin or insulin analog from the MMA chromatography matrix to provide an eluant; and (d) applying the eluant to a reverse phase high performance liquid chromatography (RP-HPLC) matrix in the presence of a water miscible organic modifier at a first concentration and eluting the properly folded insulin or insulin analog from the RP-HPLC matrix at a second concentration of water miscible organic modifier sufficient to elute the properly folded insulin or insulin analog from the RP-HPLC matrix to provide a mixture comprising the isolated properly folded insulin or insulin analog substantially free of process impurities. In particular embodiments, the aqueous solution further comprises a protease inhibitor, which may in particular embodiments be aprotinin.

In particular embodiments, the RP-HPLC is performed with a silica-based reverse phase resin in the presence of a water miscible organic modifier.

In a further embodiment, the RP-HPLC comprises a linear gradient of the water miscible organic modifier at an elevated temperature to provide a mixture comprising the isolated properly folded insulin or insulin analog substantially free of process impurities.

In a particular embodiment, the RP-HPLC comprises a linear gradient comprising the water miscible organic modifier increasing in a concentration from about 13 to 15 percent by volume to about 25 to 27 percent by volume.

In a particular embodiment, the RP-HPLC matrix comprises a linear gradient comprising the water miscible organic modifier increasing in a concentration from about 13 to 17 percent by volume to about 18 to 19 percent by volume.

In a particular embodiment, the RP-HPLC matrix comprises a linear gradient comprising the water miscible organic modifier increasing in a concentration from about 16.5 to 17.5 percent by volume to about 18 to 19 percent by volume.

In a particular embodiment, the RP-HPLC matrix comprises a first volume of a first linear gradient of the water miscible organic modifier increasing in concentration from about 13 to 17 percent by volume and a second volume of a second linear gradient from about 17 to 18.5 percent by volume of the water miscible organic modifier to provide a mixture of the properly folded insulin or insulin analog.

In a particular embodiment, the RP-HPLC has an outlet temperature greater than room temperature or between 30° C. to 50° C.; or greater than 30° C.; greater than 40° C.; or a temperature between 40° C. to 46° C.; or about 43° C.

In a particular embodiment, the water miscible organic modifier is isopropanol.

In particular embodiments, the MMA chromatography is performed with a resin comprising cross-linked agarose conjugated to N-benzyl-N-methyl ethanolamine.

In a further embodiment, the first wash buffer has a pH of about 7.8 to 8.2 or about 8.0; the second wash buffer has a pH of about 8.8 to 5.2 or about 5.0; and the eluting solution buffer has a pH of about 3.4 to 3.6 or about 3.5.

In any one of the above embodiments of the present invention disclosed herein, the insulin or insulin analog may have an isoelectric point from 4.5 to 8.5. In further embodiments, the insulin analog is insulin lispro; insulin glargine; insulin aspart; insulin glulisine, insulin, $21^A$-glycine-$30^B$-L-arginine; insulin, $21^A$-glycine; insulin $21^A$-glycine-des-$30^B$-threonine; or insulin, des-$30^B$-threonine.

Definitions

As used herein, the term "insulin" means the active principle of the pancreas that affects the metabolism of carbohydrates in the animal body and which is of value in the treatment of diabetes mellitus. The term includes synthetic and biotechnologically derived products that are the same as, or similar to, naturally occurring insulins in structure, use, and intended effect and are of value in the treatment of diabetes mellitus.

The term "insulin" or "insulin molecule" is a generic term that designates the 51 amino acid heterodimer comprising the A-chain peptide having the amino acid sequence shown in SEQ ID NO: 1 and the B-chain peptide having the amino acid sequence shown in SEQ ID NO: 2, wherein the cysteine residues a positions 6 and 11 of the A chain are linked in a disulfide bond, the cysteine residues at position 7 of the A chain and position 7 of the B chain are linked in a disulfide bond, and the cysteine residues at position 20 of the A chain and 19 of the B chain are linked in a disulfide bond. The insulin may be a heterodimer or a single chain insulin.

The term "insulin analog" as used herein includes any heterodimer or single chain analog that comprises one or more modification(s) of the native A-chain peptide and/or B-chain peptide. Modifications include but are not limited to substituting an amino acid for the native amino acid at a position selected from A4, A5, A8, A9, A10, A12, A13, A14, A15, A16, A17, A18, A19, A21, B1, B2, B3, B4, B5, B9, B10, B13, B14, B15, B16, B17, B18, B20, B21, B22, B23, B26, B27, B28, B29, and B30; and/or deleting any or all of positions B1-4 and B26-30. Insulin analogues include molecules having one to 10 amino acids at the N or C terminus of the A-chain peptide and/or B-chain peptide. Insulin analogs further include molecules amidated at the C-terminus of the A-chain peptide and/or B-chain peptide. Examples of insulin analogs include but are not limited to the heterodimer analogs disclosed in published international application WO20100080606, WO2009/099763, and WO2010080609, the disclosures of which are incorporated herein by reference. Insulin glargine (Gly(A21), Arg(B31), Arg(B32)-human insulin and insulin lispro (Lys(B28), Pro (B29) are examples of commercially available insulin analogs.

The term "insulin analogs" further includes heterodimer or single chain molecules that have little or no detectable activity at the insulin receptor or which have been modified to include one or more amino acid modifications or substitutions to have an activity at the insulin receptor that has at least 1%, 10%, 50%, 75%, or 90% of the activity at the insulin receptor as compared to native insulin. In particular aspects, the insulin analog is a partial agonist that has from 2× to 100× less activity at the insulin receptor as does native insulin. In other aspects, the insulin analog has enhanced activity at the insulin receptor.

The term "properly folded" refers to insulin or insulin analogs in which the cysteine residues a positions 6 and 11 of the A chain are linked in a disulfide bond, the cysteine residues at position 7 of the A chain and position 7 of the B chain are linked in a disulfide bond, and the cysteine residues at position 20 of the A chain and 19 of the B chain are linked in a disulfide bond.

The term "pharmaceutically pure" refers to an insulin or insulin analog that is greater than 99 percent pure with respect to contaminating macromolecules, particularly other proteins and nucleic acids, and free of infectious and pyrogenic agents.

BRIEF DESCRIPTION OF THE DRAWINGS

FIG. 1 shows absorbance (AU) tracings of the product digest pool, MMA chromatography elution fractions, and the RP-HPLC elution peak fractions in the purification of insulin lispro and how each chromatography step effects a significant reduction in process-related impurities.

DETAILED DESCRIPTION OF THE INVENTION

A key challenge with the purification of insulin (and other insulin analogs) is the downstream removal of process related impurities arising from miscleavage or insufficient cleavage of the propeptide-insulin or insulin analog precursor molecule during the enzymatic digest that follows the refolding of the precursor to provide a properly folded propeptide-insulin or insulin analog precursor.

The present invention comprises the use of two orthogonal chromatographic purification steps in tandem following enzymatic digestion of the properly folded propeptide-insulin or insulin analog precursor to remove specific product impurities such as N-terminal propeptide leader and/or signal sequences, C-peptide, dipeptides, aggregated insulin, deamidated insulin, miscleaves, misfolds, and any remaining proinsulin; improve process consistency; and increase process redundancy in the purification of the properly folded insulin or insulin analog. The process has been exemplified with insulin lispro; however, the process may be used to purify properly folded native insulin or insulin analogs such as pI-shifted insulin analogs, for example, insulin glargine; insulin aspart; insulin glulisine, insulin, $21^A$-glycine-$30^B$-L-arginine; insulin, $21^A$-glycine; insulin $21^A$-glycine-des-$30^B$-threonine; or insulin, des-$30^B$-threonine. The process has been exemplified with insulin lispro as a heterodimer; however, the process may be used to purify properly folded single-chain insulin analogs.

In the purification process, the two orthogonal chromatographic steps are performed in tandem and following the enzymatic digestion of the properly folded propeptide-insulin precursor. The orthogonal chromatography purification steps in tandem comprise (i) a chromatography step that separates molecules based upon the change in the net charge of the molecules relative to each other during the chromatography and (ii) a chromatography step that separates molecules based upon their hydrophobic interaction with the chromatography matrix. Chromatography that separates molecules based upon net charge of the molecules include anion exchange (AEX) chromatography, cation exchange (CEX) chromatography, hydroxyapatite chromatography, and mixed mode anion exchange (MMA) chromatography. Chromatography that separates molecules based upon their hydrophobic interaction with the matrix includes reverse phase high pressure liquid chromatography (RP-HPLC) and hydrophobic interaction chromatography (HIC). Each chromatography step may independently be step chromatography, gradient chromatography, or batch chromatography.

In a particular embodiment, the orthogonal chromatography purification steps in tandem comprise (i) a chromatography step that separates molecules based upon the change in net charge of the molecules relative to each other during the chromatography comprising initiating the chromatography at a pH greater than the pI of the desired molecule (e.g., the properly folded insulin or insulin analog) to enable the chromatography matrix to bind the desired molecule and recovering the desired molecule at a pH less than the pI of the desired molecule sufficient to elute the desired molecule from the matrix and (ii) a chromatography step that separates molecules based upon hydrophobic interaction. Chromatography that separates molecules based upon the change in the net charge of the desired molecule from negative to positive during the course of the chromatography include anion exchange (AEX) chromatography, hydroxyapatite) chromatography, and mixed mode anion exchange (MMA) chromatography. Chromatography that separates molecules based upon their hydrophobic interaction with the matrix includes reverse phase high pressure liquid chromatography (RP-HPLC) and hydrophobic interaction chromatography (HIC). Each chromatography step may independently be step chromatography, gradient chromatography, or batch chromatography.

In a particular embodiment, the orthogonal chromatography purification steps in tandem comprise (i) a chromatography step that separates molecules based upon the change in net charge of the molecules relative to each other during the chromatography comprising initiating the chromatography at a pH less than the pI of the desired molecule (e.g., the properly folded insulin or insulin analog) to enable the chromatography matrix to bind the desired molecule and recovering the desired molecule at a pH greater than the pI of the desired molecule sufficient to elute the desired molecule from the matrix and (ii) a chromatography step that separates molecules based upon hydrophobic interaction. Chromatography that separates molecules based upon the change in the net charge of the desired molecule from negative to positive during the course of the chromatography include cation exchange (CEX) chromatography. Chromatography that separates molecules based upon their hydrophobic interaction with the matrix includes reverse phase high pressure liquid chromatography (RP-HPLC) and hydrophobic interaction chromatography (HIC). Each chromatography step may independently be step chromatography, gradient chromatography, or batch chromatography.

In one embodiment of the invention, an aqueous solution comprising insulin or an insulin analog following enzymatic digestion to remove process-related impurities is subjected to MMA chromatography step and to a RP-HPLC step to produce a solution of the insulin or insulin that meets final drug substance quality targets.

In one aspect, the first chromatography step comprises applying an aqueous solution from the enzymatic digestion comprising the insulin or insulin analog (digest pool) to a MMA chromatography matrix. The MMA chromatography reduces the amount of product impurities that may be generated during the enzymatic digest (miscleavages and excised fragments on the propeptide-insulin precursor molecule), as well as the digest enzymes trypsin and carboxypeptidase B and any host-related impurities, e.g., protein, DNA, endotoxin. In particular aspects, the MMA chromatography matrix may be a resin comprising cross-linked agarose conjugated to N-benzyl-N-methyl ethanolamine, for example CAPTO ADHERE, available from GE Healthcare Life Sciences, Pittsburgh, Pa. The chromatography may be performed in a column format or in a batch format.

In general, the digest pool comprising the properly folded insulin or insulin analog following the enzymatic digest and the chromatography equilibration solution are both at a pH greater than the pI of the properly folded insulin or insulin analog at the time the digest pool is applied to the MMA chromatography matrix. In particular embodiments, a protease inhibitor is added to the digest pool prior to application of the digest pool to the MMA chromatography matrix. An example of a suitable inhibitor is aprotinin. Following application of the digest pool to the chromatography matrix, the insulin or insulin analog binds the MMA chromatography matrix and the matrix is washed with a first wash solution at a pH greater than the pI of the insulin or insulin analog followed by a second wash solution at a pH less than the pH of the first wash solution but greater than the pH needed to elute the insulin or insulin analog from the matrix to remove the majority of the impurities generated by the enzymatic digest. In particular embodiments, the equilibration solution and the first wash solution each comprise a first buffer and the second wash comprises a second buffer. For example, the column equilibration and first wash may comprise about 40 to 60 mM, or 45 to 55 mM, or about 50 mM sodium borate; the second wash solution may comprise about 90 to 110 mM, or about 100 mM sodium citrate.

The insulin or insulin analog is then eluted from the matrix using an aqueous elution solution at a pH sufficient to remove the insulin or insulin analog bound to the matrix, to provide an eluent comprising the insulin or insulin analog. Elution may be monitored by monitoring UV absorbance. In particular embodiments, the elution solution comprises the second buffer. For example, the elution solution may comprise about 90 to 110 mM, or about 100 mM sodium citrate.

In a further aspect of the first chromatography step, the digest pool comprising the properly folded insulin or insulin analog following the enzymatic digest and the chromatography equilibration solution are both at a pH between about 7.0 to 9.0, or pH 7.8 to 8.2, or about pH 8.0 at the time the digest pool is applied to the MMA chromatography matrix. In particular embodiments, a protease inhibitor is added to the digest pool prior to application of the digest pool to the MMA chromatography matrix. An example of a suitable inhibitor is aprotinin.

Following application of the digest pool to the chromatography matrix, the insulin or insulin analog binds the MMA chromatography matrix and the matrix is washed with a first wash solution at a pH between about 7.0 to 9.0, or pH 7.8 to 8.2, or about pH 8.0 followed by a second wash solution at a pH between about 4.0 to 6.0, or pH 4.8 to 5.2, or about pH 5.0 to remove the majority of the impurities generated by the enzymatic digest. In particular embodiments, the equilibration solution and the first wash solution each comprise a first buffer and the second wash comprises a second buffer. For example, the column equilibration and first wash may comprise about 40 to 60 mM, or 45 to 55 mM, or about 50 mM sodium borate; the second wash solution may comprise about 90 to 110 mM, or about 100 mM sodium citrate.

The insulin or insulin analog is then eluted from the matrix using an aqueous elution solution at pH between about 3.0 to 4.0, or pH 3.4 to 3.6, or about 3.5, to provide an eluent comprising the insulin or insulin analog. Elution may be monitored by monitoring UV absorbance. In particular embodiments, the elution solution comprises the second buffer. For example, the elution solution may comprise about 90 to 110 mM, or about 100 mM sodium citrate.

In another embodiment of the invention, an aqueous solution comprising insulin or an insulin analog following enzymatic digestion to remove process-related impurities is subjected to AEX chromatography step and to an RP-HPLC step to produce a solution of the insulin or insulin that meets final drug substance quality targets.

In one aspect, the first chromatography step comprises applying an aqueous solution from the enzymatic digestion comprising the insulin or insulin analog (digest pool) to a AEX chromatography matrix. The AEX chromatography reduces the amount of product impurities that may be generated during the enzymatic digest (miscleavages and excised fragments on the propeptide-insulin precursor molecule), as well as the digest enzymes trypsin and carboxypeptidase B and any host-related impurities, e.g., protein, DNA, endotoxin. In particular aspects, the AEX chromatography matrix may be a resin comprising cross-linked agarose conjugated to DEAE (diethylaminoethyl), for example DEAE SEPHAROSE FAST FLOW, available from GE Healthcare Life Sciences or Q HYPER D, available from Pall Corporation, Port Washington. N.Y. The chromatography may be performed in a column format or in a batch format.

In general, the digest pool comprising the properly folded insulin or insulin analog following the enzymatic digest and the chromatography equilibration solution are both at a pH greater than the pI of the properly folded insulin or insulin analog at the time the digest pool is applied to the AEX chromatography matrix. In particular embodiments, a protease inhibitor is added to the digest pool prior to application of the digest pool to the AEX chromatography matrix. An example of a suitable inhibitor is aprotinin. Following application of the digest pool to the chromatography matrix, the insulin or insulin analog binds the AEX chromatography matrix and the matrix is washed with a first wash solution at a pH greater than the pI of the insulin or insulin analog followed by a second wash solution at a pH less than the pH of the first wash solution but greater than the pH needed to elute the insulin or insulin analog from the matrix to remove the majority of the impurities generated by the enzymatic digest. In particular embodiments, the equilibration solution and the first wash solution each comprise a first buffer and the second wash comprises a second buffer. For example, the column equilibration and first wash may comprise about 40 to 60 mM, or 45 to 55 mM, or about 50 mM sodium borate; the second wash solution may comprise about 90 to 110 mM, or about 100 mM sodium citrate.

The insulin or insulin analog is then eluted from the matrix using an aqueous elution solution at a pH sufficient to remove the insulin or insulin analog bound to the matrix, to provide an eluent comprising the insulin or insulin analog. Elution may be monitored by monitoring UV absorbance. In particular embodiments, the elution solution comprises the second buffer. For example, the elution solution may comprise about 90 to 110 mM, or about 100 mM sodium citrate.

In a further aspect of the first chromatography step, the digest pool comprising the properly folded insulin or insulin analog following the enzymatic digest and the chromatography equilibration solution are both at a pH between about 7.0 to 9.0, or pH 7.8 to 8.2, or about pH 8.0 at the time the digest pool is applied to the AEX chromatography matrix. In particular embodiments, a protease inhibitor is added to the digest pool prior to application of the digest pool to the AEX chromatography matrix. An example of a suitable inhibitor is aprotinin.

Following application of the digest pool to the chromatography matrix, the insulin or insulin analog binds the AEX chromatography matrix and the matrix is washed with a first wash solution at a pH between about 7.0 to 9.0, or pH 7.8 to 8.2, or about pH 8.0 followed by a second wash solution at a pH between about 4.0 to 6.0, or pH 4.8 to 5.2, or about pH 5.0 to remove the majority of the impurities generated by the enzymatic digest. In particular embodiments, the equilibration solution and the first wash solution each comprise a first buffer and the second wash comprises a second buffer. For example, the column equilibration and first wash may comprise about 40 to 60 mM, or 45 to 55 mM, or about 50 mM sodium borate; the second wash solution may comprise about 90 to 110 mM, or about 100 mM sodium citrate.

The insulin or insulin analog is then eluted from the matrix using an aqueous elution solution at pH between about 3.0 to 4.0, or pH 3.4 to 3.6, or about 3.5, to provide an eluent comprising the insulin or insulin analog. Elution may be monitored by monitoring UV absorbance. In particular embodiments, the elution solution comprises the second buffer. For example, the elution solution may comprise about 90 to 110 mM, or about 100 mM sodium citrate.

The second chromatography step comprises applying the eluent from the first chromatography step to an RP-HPLC matrix in a column format to remove the remainder of the digest-related and non-digest-related product impurities (e.g., trisulfide-containing species, correct molecular weight misfolds, deamidated species, aggregates) and further reduce host-related impurities to meet final drug substance quality targets.

The reverse phase high performance liquid chromatography may be performed with a temperature stable and pressure stable organic modified chromatography material or matrix. The material may be a lipophilically modified silica gel to which a hydrophobic matrix has been applied. Examples of a hydrophobic matrix are alkanes with a chain length of from 3 to 20 carbon atoms, in particular 8 to 18 carbon atoms. Additionally, the particle size can vary within a wide range, for example from 5 to 300 μm or 5 to 60 μm, in particular from 10 to 50 μm. The pore width can also vary within a wide range; favorable pore widths are from 50 to 300 Å, in particular 100 to 200 Å. Examples of lipophilically modified silica gel materials are: NUCLEOSIL, Macherey & Nagel GmbH+Co.KG, Duren, Germany spherical and non-spherical materials of various particle size up to 45 μm, 100 Å pore width, C8- or C18-modified; LICHROPREP, E. Merck Co., Darmstadt, Germany non-spherical and spherical materials of various particle sizes up to μm, 60-250 Å pore width, C8- or C18-modified; LICHROSPHER SELECT B, E. Merck Co., Darmstadt, Germany spherical material up to 25 μm particle size, C8-modified; WATERS PREP, Millipore GmbH, Eschborn, Germany C18-modified, 50-105 μm non-spherical, 100 Å pore width; ZORBAX PRO10, DuPont de Nemours (Germany) GmbH, Bad Homburg, Germany C8-modified, 10 μm, spherical, 100 Å pore width; and KROMASIL, EKA Nobel Co., Nobel Industries, Sweden C4-, C8- and C18-modified, up to 20 μm, spherical, 100, 150 or 200 Å pore width. In particular aspects, the chromatography material is a silica-based reverse phase resin modified with hydrocarbon chains about 8 carbons in length. In a further aspect, the chromatography material is KROMASIL C8-modified. The chromatography may be performed in a column format or in a batch format.

In general, the eluent from the first chromatography step is diluted with a water miscible organic modifier or solvent to a final concentration that enables the insulin or insulin analog to bind to the RP-HPLC matrix. Typically, the concentration of the water miscible organic modifier is about 5% v/v. In particular aspects, the water miscible modifier is isopropanol. The RP-HPLC matrix is equilibrated with a solution containing a buffer at a pH of about 3.1 and the water miscible organic modifier and maintained at an outlet temperature greater than room temperature. After applying the diluted eluent to the RP-HPLC matrix, the RP-HPLC matrix is washed with a first wash solution containing the buffer at a pH of about 3.1 and the water miscible organic modifier at an outlet temperature greater than room temperature. The RP-HPLC matrix is then washed with a linear gradient comprising the buffer at pH 3.1 and ranging from about 5% to a concentration near to but not at the concentration sufficient to elute the bound insulin or insulin analog from the RP-HPLC matrix at an outlet temperature greater than room temperature. In particular embodiments, the linear gradient may be from about 5% to about 13% of the water miscible organic modifier. The insulin or insulin analog, which is bound to the RP-HPLC matrix, is eluted from the RP-HPLC matrix using a linear gradient of the water miscible organic modifier in the buffer at an outlet temperature greater than room temperature. In one embodiment, the linear gradient is from about 13% to about 15% to about 25% to about 27%. In another embodiment, the linear gradient is from about 13% to 17% to about 18% to about 19%. In a further embodiment, the linear gradient is from about 16.5% to about 17.5% to about 18% to about 19%. In a further embodiment, two sequential linear gradients are used. The first linear gradient is about 13% to about 17% of a first volume. The second linear gradient is about 17% to about 18.5% at the same volume or a second volume. For example the first volume may be about two column volumes and the second volume may be about four to five column volumes. During elution, fractions are collected and the amount of insulin or insulin analog eluted is monitored by measuring UV absorbance at A254 or A295 and the fractions containing the insulin or insulin analog are combined for crystallization.

In particular embodiments, the first volume may be about two column volumes and the second volume may be about four to five column volumes.

In particular aspects, the protein concentration of the diluted eluent is about 20 g/L or less. In particular aspects, the water miscible solvent or modifier is isopropanol. In particular aspects, the buffer may be for example, about 100 mM acetic acid. In particular embodiments, the RP-HPLC has an outlet temperature greater than room temperature or between 30° C. to 50° C.; or greater than 30° C.; greater than 40° C.; or a temperature between 40° C. to 46° C.; or about 43° C.

In a further embodiment of the second chromatography step, the eluent from the first chromatography step is diluted with a water miscible organic modifier or solvent to a final concentration of about 5% of the water miscible modifier and a protein concentration of about 20 g/L or less. In particular aspects, the water miscible modifier is isopropanol. The column comprising the RP-HPLC matrix is equilibrated with a solution at a pH of about 3.1 and 5% of a water miscible organic solvent and maintained at a temperature of about 40° C. After applying the diluted eluent to the column, the column is washed with about two column volumes or more of a first wash solution at a pH of about 3.1 and 5% of a water miscible organic solvent at 40° C. The column is then washed with about 0.4 to 0.6 column volume of a gradient at pH 3.1 and ranging from 5% to 13% of a water miscible organic solvent at 40° C. In one embodiment, the linear gradient is from about 13% to about 15% to about 25% to about 27%. In another embodiment, the linear gradient is from about 13% to 17% to about 18% to about 19%. In a further embodiment, the linear gradient is from about 16.5% to about 17.5% to about 18% to about19%. In a further embodiment, two sequential linear gradients are used. The first linear gradient is about 13% to about 17% of a first volume. The second linear gradient is about 17% to about 18.5% at the same volume or a second volume. For example the first volume may be about two column volumes and the second volume may be about four to five column volumes. During elution, fractions are collected and the amount of insulin or insulin analog eluted is monitored by measuring UV absorbance at A254 or A295 and the fractions containing the insulin or insulin analog are combined for crystallization.

The following examples are intended to promote a further understanding of the present invention.

EXAMPLE 1

The MMA chromatography step removes trypsin, carboxypeptidase B, and product-related impurities generated by the enzymatic digest. The MMA chromatography step uses CaptoAdhere resin, from GE Healthcare, packed to a target bed height of ~20 cm and a column volume (CV) of 90 L. Prior to packing, the resin storage solution (20% ethanol) is decanted and replaced with an equal volume of 0.1 N NaOH. The settled resin is re-suspended in this buffer. Settling, decanting, and re-suspension are repeated two more times. Next, the settled resin is diluted to achieve the defined slurry percentage (experience with 60-70%). The resin slurry is transferred to the column and flow packed using 0.1 N NaOH. A continuous increase in flow through the column is performed (up to 45 LPM) until a >3 bar pressure drop across the column is achieved.

Feed preparation for MMA occurs during the enzymatic digest step. The final volume of the MMA feed is approximately 3000-3500 L and is held at 15° C. before processing and warmed in-line to 21° C. during loading onto MMA. The MMA feed is passed through a 0.2 μm guard filter to prevent plugging and over-pressurization of the column and to provide additional bioburden control to the process.

Loading of the feed begins once the column outlet temperature is verified to be stable at ~21° C. Additionally, 0.2 μM guard filters are used prior to loading to protect the column and provide an additional control point for bioburden. The two wash steps remove the majority of the impurities generated by the enzymatic digest. Product collection begins when the 280 nm UV signal increases to 1.5 CU. The end of collection is UV-based; collection stops when the 280 nm UV signal reaches 1.5 CU. The MMA pool is collected into a chilled heel of RP Buffer A (100 mM Acetic Acid, pH adjusted to 3.1 with 50% ammonium hydroxide) to maintain product solubility at 2-8° C.; reduced temperature is required to reduce product aggregation and deamidation. The combined MMA pool comprises approximately 4000 L (approximately 1000 L per cycle). At the completion of the batch, the MMA pool is well mixed, sampled and assayed for insulin lispro concentration.

The purpose of the Reverse Phase Chromatography step is to remove residual product-related impurities such as correct molecular weight misfolded forms, enzymatic miscleavages, deamidated product, and aggregates.

Kromasil® C8 silica based reverse phase resin is available as bulk through the manufacturer.

The RP Kromasil® C8 resin is packed, using a dynamic axial compression (DAC) system, to a target bed height of ~25 cm. The required amount of resin (600 g of dry resin powder will yield a packed volume of 1 L) is weighed out and poured into a vessel containing 3 L of isopropanol (IPA) per kg of dry resin. This slurry is then transferred into the column using a diaphragm pump. The column piston is lowered and the column is packed to a target pressure of 70 bar. The column is equilibrated at 40° C., initially with 5% Buffer B (95% Buffer A: 100 mM acetate, pH 3.1; 5% IPA) and then with 70% B (30% A; 70% IPA), in preparation for column performance (pulse) testing. The column outlet temperature is controlled by an inline heat exchanger and column jacket. After the column is successfully packed, the column is conditioned and flushed, prior to first use, in order to remove resin leachables as well as residual air from the pores of the resin. At the end of the flushing procedure, the column is stored in a solution of 30% Buffer A and 70% Buffer B prepared inline using the chromatography skid.

For processing, the RP feed is prepared by diluting (in-line) the MMA Product Pool with 5% (v/v) isopropanol (IPA). The feed is processed via multiple column cycles, typically 2-3, targeting a load factor of ≤20 g/L. During the process, UV Absorbance is monitored at 254 and 295 nm. The two wavelengths will be evaluated during the engineering run to determine the appropriate primary wavelength for product collection. First, the column is equilibrated to ensure a stable baseline temperature and absorbance reading. During equilibration, the inline heat exchanger parameters are set to target a column outlet temperature of 40° C. The column is then loaded with diluted MMA pool to the defined load factor and then washed prior to elution. Elution is accomplished using two sequential gradients of increasing IPA (13-18.5% Buffer B) and the product is collected, based on the A254 or A295 profile, into a chilled WFI heel to reduce the IPA concentration in the product stream to below 10%. The material eluting on either side of the main product peak is collected as six ~20 L fractions (volume after dilution; 3 pre- and 3 post-main peak fractions). Pooling of the adjacent fractions with the main product peak may be performed after the analysis of each fraction for each cycle has been completed for concentration and purity by the UPLC-48 assay. Fractions are added to the main peak in order to target a final pool purity using the calculated UPLC-48 concentration, total impurity, A21 desamido lispro, and the individual impurity percentages measured. The fractions comprising the main peak may be crystallized using methods known in the art and the crystals dried.

FIG. 1 shows absorbance (AU) tracings of the product digest pool, MMA chromatography elution fractions, and the RP-HPLC elution peak fractions in the purification of insulin lispro and shows how each chromatography step effects a significant reduction in process-related impurities.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed:

1. A process for isolating properly folded insulin or insulin analog from process related impurities, wherein the process comprises:
    subjecting an aqueous solution comprising properly folded precursor insulin or insulin analog that has been enzymatically digested to produce properly folded insulin or insulin analog and process related impurities to two orthogonal chromatography purification steps in tandem to separate the isolated properly folded insulin or insulin analog from the process related impurities;
    wherein the two orthogonal chromatography purification steps in tandem comprise (i) a mixed mode anion exchange (MMA) chromatography step performed with a resin comprising cross-linked agarose conjugated to N-benzyl-N-methyl ethanolamine or an anion exchange (AEX) chromatography step performed with a resin comprising agarose conjugated to DEAE and (ii) an RP-HPLC step performed with a silica-based reverse phase resin in the presence of a water miscible organic modifier; and, wherein the MMA or AEX chromatography comprises
(i) applying to the MMA or AEX chromatography matrix the aqueous solution in which properly folded precursor insulin or insulin analog has been enzymatically digested to produce the properly folded insulin or insulin analog;
(ii) washing the MMA or AEX chromatography matrix with a first wash solution comprising a buffer at a basic pH and then washing the MMA or AEX chromatography matrix with a second wash solution comprising a buffer at an acidic pH greater than or higher than the pH capable of eluting the properly folded insulin or insulin analog from the MMA or AEX chromatography matrix; and
(iii) eluting the properly folded insulin or insulin analog from the MMA or AEX chromatography matrix with an eluting solution comprising a buffer at an acidic pH sufficient to elute the properly folded insulin or-insulin analog from the MMA or AEX chromatography matrix to provide a mixture of the properly folded insulin or insulin analog for the RP-HPLC step.

2. The process of claim 1, wherein the RP-HPLC comprises eluting the properly folded insulin or insulin analog with a linear gradient of a water miscible organic modifier.

3. The process of claim 1, wherein the insulin or insulin analog has an isoelectric point from 4.5 to 8.5.

4. The process of claim 1, wherein the insulin analog is insulin lispro; insulin glargine; insulin aspart; insulin glulisine, insulin, $21^A$-glycine-$30^B$-L-arginine; insulin, $21^A$-glycine; insulin $21^A$-glycine-des-$30^B$-threonine; or insulin, des-$30^B$-threonine.

* * * * *